United States Patent [19]

Ogata et al.

[11] Patent Number: 4,888,329
[45] Date of Patent: Dec. 19, 1989

[54] ANTIULCER COMPOSITION

[75] Inventors: Kazumi Ogata, Toyonaka; Takahiro Ogawa, Nishinomiya; Takahiro Sakaue, Itami, all of Japan

[73] Assignee: Senju Pharmaceutical Co., Ltd., Osaka, Japan

[21] Appl. No.: 187,032

[22] Filed: Apr. 27, 1988

[30] Foreign Application Priority Data

Apr. 28, 1987 [JP] Japan ................... 62-106077

[51] Int. Cl.$^4$ ........................... A61K 31/665
[52] U.S. Cl. ..................... 514/100; 514/927
[58] Field of Search ........................... 514/100

[56] References Cited

U.S. PATENT DOCUMENTS 4,564,686 1/1986 Ogata ................... 549/220

Primary Examiner—Frederick E. Waddell
Attorney, Agent, or Firm—Wenderoth, Lind & Ponack

[57] ABSTRACT

A composition comprising a compound of the following formula or a salt thereof

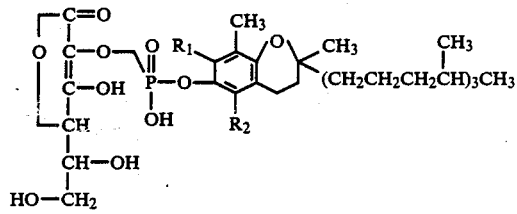

wherein $R_1$ and $R_2$ each represent a hydrogen atom or a methyl group. The composition is highly safe and useful as an antiulcer agent.

1 Claim, No Drawings

ANTIULCER COMPOSITION

BACKGROUND OF THE INVENTION

1. Field of the Invention

The present invention relates to a novel antiulcer agent.

2. Description of the Prior Art

The incidence of peptic ulcer disease due to the intake of pharmaceuticals or alcoholic beverages and particularly arising from mental stresses has been increasing year by year and a variety of drugs for combating this disease are being explored and developed. However, the drugs heretofore available have strong side effects or suffer from a gradual loss of efficacy after repeated use or may result in ulcer recurrence after treatment is discontinued. Thus, we do not know of a presently employed drug that is ideal.

These circumstances have been responsible for a strong demand for an antiulcer drug free of the above-mentioned shortcomings.

SUMMARY OF THE INVENTION

The present invention is directed to an antiulcer composition comprising a compound of the following formula or a pharmaceutically acceptable salt thereof

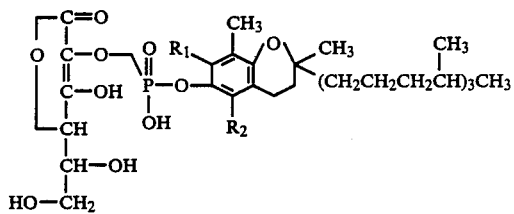

wherein $R_1$ and $R_2$ each represents a hydrogen or a methyl group.

DETAILED DESCRIPTION OF THE INVENTION

The compound included as an active ingredient in the antiulcer composition of the invention is phosphoric acid diester of L-ascorbic acid and $\alpha$, $\beta$, $\gamma$ or $\delta$-tocopherol.

$\alpha$, $\beta$, $\gamma$ and $\delta$-Tocopherol are known compounds having vitamin E activity, while ascorbic acid is known to be effective against scurvy. Both have been widely used as medicines having such activities, and the latter, ascorbic acid, has been used as an antioxidant for food and other products by taking advantage of its antioxidative activity.

The compound employed in the present invention is already known as a prophylactic and therapeutic agent for the treatment of cataracts and climacteric disturbance (Japanese Patent Kokai 59-219295 corresponding to U.S. Pat. No. 4,564,686) but its effectiveness against peptic ulcer is not known.

We investigated the antiulcer activity of various compounds and found that compounds of the general formula

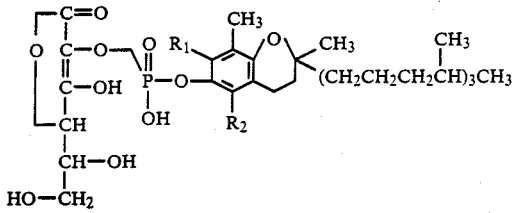

wherein $R_1$ and $R_2$ each is a hydrogen atom or a methyl group and salts thereof (hereinafter referred to collectively as the compound of the invention) are very effective for the treatment of peptic ulcers. The present invention is based on the above finding.

The present invention provides a novel antiulcer composition.

As is obvious from its chemical structure, the compound of the invention is a compound constructed by coupling ascorbic acid to tocopherol through phosphoric acid. Because the compound exhibits antiinflammatory activity, this compound has been demonstrated to be effective as a therapeutic agent for hemorrhoids and as an antirheumatic agent.

The compound of the invention can be produced by the methods described in, among others, Japanese Patent Kokai 59-219295 and Japanese Patent Application 61-46878 (corresponding to copending U.S. patent application Ser. No. 21,655, filed Mar. 4, 1987).

The active ingredient of the present antiulcer composition shows very low toxicity. For instance, the toxicity in rat of disodium salt of phosphoric acid diester of L-ascorbic acid and DL-$\alpha$-tocopherol was observed as follows:

| $LD_{50}$ | |
|---|---|
| Per os | >10,000 mg/kg |
| Subcutaneous administration | 793 mg/kg |

In the production of the antiulcer composition of the invention, the compound of the invention, either the free acid or a salt thereof, is processed into dosage forms suitable for administration. The salt may, for example, be the sodium salt, potassium salt, magnesium salt or calcium salt, and any of them can be used for purposes of the invention.

The composition of the invention can be administered orally or parenterally. For oral administration, it may be formulated into tablets, capsules, powders, granules or any other form appropriate for oral use. For parenteral administration, it may be preferably formulated into an injectable preparation.

The amount of the compound of the invention in such an antiulcer composition varies with the dosage form selected, symptoms to be treated and so on. By way of example, injections preferably contain about 0.01 to 10 (W/V)% of the compound. Oral preparations are formulated so as to provide a daily dosage of about 100 to 1000 mg per adult.

Formulation of the compound of the invention can be carried out by procedures known per se. For example, tablets are usually prepared by the following procedure. The compound of the present invention is first rendered granular with or without uniform admixture with a diluent (e.g. lactose), binder (e.g. syrup, gum arabic, gelatin, sorbitol, tragacanth, polyvinylpyrrolidone), disintegrator (e.g. potato starch), and other suitable additives. These granules are usually prepared by compressing the compound of the present invention or the aforesaid mixtures, and crushing to granules, or by adding moistening agent (e.g. sodium lauryl sulfate) to the present compound or the mixture, granulating and drying. The resultant granules are provided with additives such as a lubricant (e.g. magnesium stearate, talc, polyethyleneglycol, silica), and compressed into a desired shape and size. Or, in case of preparing injectable solution, the sodium or potassium salt of the compound of the invention is dissolved or suspended in distilled water and after adjustment to a pH approximating that of body fluid (about 4–10, preferably 5–9) with hydrochloric acid, acetic acid or the like as required and addition of an isotonizing agent (e.g sorbitol, glycerol, polyethylene glycol, propyl glycol, glucose and sodium chloride), the solution is aseptically filtered to give an injection.

Unless contrary to the purpose of the invention, the antiulcer composition of the invention may be further formulated in combination with other drugs, such as other antiulcer agents, analgesics, nutritive agents, digestants, and so on.

The following experimental and preparation examples are further illustrative of the invention.

In the following examples, the terms "α-EPC", "β-EPC", "γ-EPC" and "δ-EPC" respectively denote the compound of the formula [I] wherein:

|  | $R_1$ | $R_2$ |
|---|---|---|
| α-EPC | $CH_3$ | $CH_3$ |
| β-EPC | $CH_3$ | H |
| γ-EPC | H | $CH_3$ |
| δ-EPC | H | H | and optical rotations of tocopherols in the respective molecules are all DL-form.

Experimental Example 1

Effect on rat stress ulcer

The test drug was administered orally to male Wistar rats weighing 230–270 g and after 30 minutes, the four limbs of each rat were fixed to a board with tying thread. The rats were then immersed in water at 23° C. for 5 hours for stress loading. Ten minutes before water immersion, 3 ml/kg of 5% Pontamine Sky Blue was intravenously injected. After this 5-hour water immersion, the rats were removed from the water and the stomach was excised and fixed in 1% aqueous formaldehyde. Then, the length of the gastric ulcer induced was measured.

The results are shown in Table 1.

TABLE 1

| Compound | doses (mg/5ml/kg) | Length of ulcer (mm) | % Inhibition |
|---|---|---|---|
| Control* | — | 25.5 ± 4.29 (6) | — |
| α-EPC** | 100 | 19.4 ± 6.91 (5) | 23.9 |
| α-EPC** | 1000 | 10.3 ± 3.51 (6) | 59.6 |

*Control: 5% gum arabic solution, 5 ml/kg
**Disodium salt

In the above table, each value in the column corresponding to length of ulcer is the mean ± S.E. (standard error) and the figure in parentheses denotes the number of the cases.

Experimental Example 2

Effect on rat stress ulcer

The test drug was aministered intraperitoneally to male Wistar rats weighing about 150 g. After 30 minutes, each rat was fixed to a board with tying thread and immersed in water at 23° C. for 7 hours for stress loading. Ten minutes before water immersion, 3 ml/kg of 5% Pontamine Sky Blue was intravenously administered.

After this 7-hour water immersion, the rats were removed from the water and the stomach was excised and fixed in 1% aqueous formaldehyde. Then, the length (mm) of the gastric ulcer induced was measured.

The results are shown in Table 2.

TABLE 2

| Compounds | doses (mg/5ml/kg) | Length of ulcer (mm) | % Inhibition |
|---|---|---|---|
| Control* | | 34.3 ± 4.76 (6) | — |
| α-EPC** | 10 | 7.7 ± 6.00 (6) | 77.6 |

*physiological saline, 5 ml/kg
**Disodium salt

In the above table, each value in the column corresponding to the length of ulcer is the mean ± S.E. and the figure in the parentheses denotes the number of cases.

Experimental Example 3

Effect on indomethacin-induced ulcer

Male Donryu rats weighing 180–200 g were fasted for 24 hours and, then, a suspension of indomethacin in 1% carboxymethylcellulose (30 mg/5 mg/kg) was subcutaneously injected. The test drug was orally administered 30 minutes before indomethacin loading. Ten minutes before sacrifice at 7 hours after indomethacin loading, 3 ml/kg 5% Pontamine Sky Blue was intravenously injected. After sacrifice, the stomach was excised and fixed in 1% aqueous formaldehyde. Then, the length (mm) of the gastric ulcer induced was measured.

The results are shown in Table 3.

TABLE 3

| Compound | doses (mg/5 ml/kg) | Length of ulcer (mm) | % Inhibition |
|---|---|---|---|
| Control* | | 30.8 ± 5.97 (9) | — |
| α-EPC** | 300 | 20.4 ± 3.72 (8) | 33.8 |
| α-EPC** | 1000 | 3.5 ± 1.54 (9) | 88.6 |

*5% gum arabic solution, 5 ml/kg
**Disodium salt

In the above table, each value in the column corresponding to the length of ulcer is the mean ± S.E. and the figure in parentheses denotes the number of cases.

Experimental Example 4

Effect on rat stress ulcer

The test drugs were administered intraperitoneally to male Wistar rats weighing about 130–190 g and after 30 minutes, the four limbs of each rat were fixed to a board with tying thread. The rats were then immersed in water at 23° C. for 7 hours for stress loading. Ten minutes before water immersion, 3 ml/kg of 5% Pontamine Sky Blue was intravenously injected. After 7-hour water immersion, the rats were removed from the water and stomach was excised and fixed in 1% aqueous formaldehyde. Then length of gastric ulcer induced was measured.

The results are shown in Table 4.

TABLE 4

| Compound | doses (mg/5 ml/kg) | Length of ulcer (mm) | % Inhibition |
|---|---|---|---|
| Control* | — | 31.7 ± 3.64 (11) | — |
| α-EPC** | 10 | 8.5 ± 4.06 (10) | 73.2 |
| α-EPC** | 30 | 2.8 ± 1.27 (5) | 91.2 |
| Cimetidine | 200 | 7.4 ± 7.16 (5) | 76.7 |

*physiological saline, 5 ml/kg
**Disodium salt

In the above table, each value in the column corresponding to length of ulcer is the mean ± S.E. and the figure in the parentheses denotes the number of cases.

As is obvious from the table 4, the compound of the present invention exhibits more potent effectiveness against gastric ulcer in lower concentration than the widely used cimetidine.

Preparation Example 1

| Tablets | |
|---|---|
| disodium salt of α-EPC | 100 mg |
| Lactose | 80 mg |
| Starch | 17 mg |
| Magnesium stearate | 3 mg |

100 g of disodium salt of EPC is first rendered granular with 17 g starch, and 80 g of lactose. The resultnt granules are provided with 3 g of magnesium stearate and compressed into tablets.

Preparation Example 2

| Injection | |
|---|---|
| Disodium salt of α-EPC | 0.02 g |
| Glucose | 5 g |
| Distilled water for injection | To make 100 ml |

To about 80 ml of distilled water for injection are dissolved 0.02 g of disodium salt of EPC and adjusted to a pH 6 with hydrochloric acid. To the resultant solution was added 5 g of glucose. The mixture is thoroughly stirred to make the total 100 ml. The solution is aseptically filtered to give an injection.

Prepration Example 3

| Tablets | |
|---|---|
| Disodium salt of δ-EPC | 300 mg |
| Lactose | 80 mg |
| Starch | 17 mg |
| Magnesium stearate | 3 mg |

Using the above materials, tablets are manufactured in the same manner as Prepration Example 1.

What is claimed is:

1. A method for the treatment of peptic ulcer, which comprises administering orally or parenterally to a patient in need of such treatment an antiulcer effective amount of a compound of the formula or a pharmaceutically acceptable salt thereof

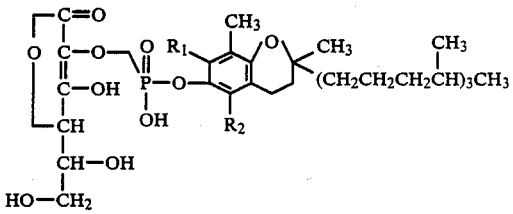

wherein $R_1$ and $R_2$ each represent hydrogen or methyl.

* * * * *